United States Patent
Tateda et al.

(10) Patent No.: US 8,195,261 B2
(45) Date of Patent: Jun. 5, 2012

(54) VITAL INFORMATION MEASURING DEVICE

(75) Inventors: Norihiro Tateda, Sakai (JP); Yoshiroh Nagai, Nishinomiya (JP)

(73) Assignee: Konica Minolta Sensing, Inc. (JP)

( * ) Notice: Subject to any disclaimer, the term of this patent is extended or adjusted under 35 U.S.C. 154(b) by 1476 days.

(21) Appl. No.: 11/595,704

(22) Filed: Nov. 10, 2006

(65) Prior Publication Data

US 2007/0112259 A1    May 17, 2007

(30) Foreign Application Priority Data

Nov. 14, 2005 (JP) ................................. 2005-329259

(51) Int. Cl.
*A61B 5/1455* (2006.01)

(52) U.S. Cl. ......... 600/310; 600/322; 600/323; 600/324

(58) Field of Classification Search .................. 600/330, 600/336, 500, 310, 322–324; 356/41
See application file for complete search history.

(56) References Cited

U.S. PATENT DOCUMENTS

| | | | | |
|---|---|---|---|---|
| 4,800,885 | A * | 1/1989 | Johnson | 600/330 |
| 4,846,183 | A * | 7/1989 | Martin | 600/336 |
| 4,942,877 | A * | 7/1990 | Sakai et al. | 600/323 |
| 4,955,379 | A | 9/1990 | Hall | 128/633 |
| 4,960,126 | A * | 10/1990 | Conlon et al. | 600/336 |
| 5,995,858 | A * | 11/1999 | Kinast | 600/323 |
| 6,397,092 | B1 * | 5/2002 | Norris et al. | 600/323 |

FOREIGN PATENT DOCUMENTS

| | | |
|---|---|---|
| JP | 1-153139 A | 6/1989 |
| JP | 03-500614 A | 2/1991 |
| JP | 04-332536 A | 11/1992 |
| JP | 11-137538 A | 5/1999 |
| JP | 2005-114678 A | 4/2005 |
| JP | 2005-304832 A | 11/2005 |

OTHER PUBLICATIONS

Japanese Notice of Reasons for Rejection dated Jul. 13, 2010, for counterpart Japanese Application No. 2005-329259, together with an English translation thereof.

* cited by examiner

*Primary Examiner* — Eric Winakur
*Assistant Examiner* — Chu Chuan Liu
(74) *Attorney, Agent, or Firm* — Cantor Colburn LLP

(57) ABSTRACT

A vital information measuring device includes: a first light emitter for outputting light having a first wavelength; a second light emitter for outputting light having a second wavelength different from the first wavelength; a light detector for detecting the light outputted from the first light emitter and the light outputted from the second light emitter; an emission controller for controlling the first light emitter and the second light emitter to emit the respective light at sampling frequencies different from each other a detection controller for controlling the light detector to detect the light from the first light emitter and the light from second light emitter in synchronism with the emission timing of the first light emitter and the emission timing of the second light emitter, respectively; and a storage for storing therein a light detection signal outputted from the light detector as measurement data.

4 Claims, 15 Drawing Sheets

PHOTOELECTRIC PULSE WAVE SIGNAL

ACCELERATION PULSE WAVEFORM
OBTAINED FROM A NORMAL HEALTHY
PERSON IN THIRTIES

ACCELERATION PULSE WAVEFORM
OBTAINED FROM A NORMAL HEALTHY
PERSON IN SIXTIES

VITAL INFORMATION MEASURING DEVICE

This application is based on Japanese Patent Application No. 2005-329259 filed on Nov. 14, 2005, the contents of which are hereby incorporated by reference.

BACKGROUND OF THE INVENTION

1. Field of the Invention

The present invention relates to a vital information measuring device for measuring vital information such as an arterial blood oxygen saturation or a pulse rate.

2. Description of the Related Art

There is used a pulse oximeter in the field of diagnosing a sleep apnea syndrome (SAS) (see U.S. Pat. No. 4,955,379 corresponding to Japanese Unexamined Patent Publication No. 1-153139/1989, for instance). The pulse oximeter has a measuring unit which is removably attached to a predetermined measurement site of a living body i.e. a subject. As shown in FIG. 14, red light and infrared light are alternately outputted at a relatively low sampling frequency e.g. 30 Hz, in other words, at a cycle of e.g. 1/30 sec toward the measurement site of the living body, with phases of the respective light displaced from each other. The amount of light transmitted through or reflected from the measurement site of the living body is detected, and an oxygen saturation ($SpO_2$) in blood of the subject is measured based on the detected light amount.

There is also known a photoelectric pulse wave sensor for acquiring a photoelectric pulse waveform to assess an arteriosclerosis index i.e. a blood vessel age, or an autonomic disorder of a subject. As shown in FIG. 15, the photoelectric pulse wave sensor is adapted to acquire a photoelectric pulse waveform by outputting light of a single wavelength or white light at a relatively high sampling frequency e.g. 120 Hz i.e. at a cycle of 1/120 sec, and by detecting the outputted light. A blood vessel age i.e. an arteriosclerosis index or a like parameter can be assessed by analyzing characteristics on the photoelectric pulse waveform.

In recent years, there is a demand for a measuring device capable of obtaining a blood oxygen saturation and a photoelectric pulse waveform for use in assessment of a blood vessel age or a like parameter in pair.

Measurements of the blood oxygen saturation and the photoelectric pulse waveform are common in detecting a change in light from a living body. Accordingly, the photoelectric pulse waveform is measurable with use of the conventional pulse oximeter. However, the pulse oximeter is designed to output red light and infrared light with a sampling frequency lower than the sampling frequency used in the photoelectric pulse wave sensor. Accordingly, the photoelectric pulse waveform obtained by the conventional pulse oximeter is used at most for judging reliability of an oxygen saturation measurement value, which is varied resulting from a variation in pulse waveform due to a body movement or the like. Thus, the conventional pulse oximeter has failed to acquire a photoelectric pulse waveform for use in assessing a blood vessel age or an autonomic disorder.

In view of the above, there is proposed an idea of outputting both red light and infrared light with a sampling frequency substantially identical to the sampling frequency of an output light required in measuring a photoelectric pulse waveform for use in assessing a blood vessel age or a like parameter to obtain a blood oxygen saturation and a photoelectric pulse waveform for use in assessing a blood vessel age or an autonomic disorder in pair. With such a configuration, however, if merely acquisition of information concerning a blood oxygen saturation is required, an output operation of unnecessary light that is not used in the acquisition of the information concerning the blood oxygen saturation is conducted, which may result in waste of power consumption.

SUMMARY OF THE INVENTION

In view of the above problems residing in the conventional examples, it is an object of the present invention to provide a vital information measuring device that enables to suppress power consumption, and to measure a blood oxygen saturation and a photoelectric pulse waveform for use in assessing a blood vessel age i.e. an arteriosclerosis index in pair.

An aspect of the invention is directed to a vital information measuring device including: a first light emitter for outputting light having a first wavelength; a second light emitter for outputting light having a second wavelength different from the first wavelength; a light detector for detecting the light outputted from the first light emitter and the light outputted from the second light emitter; an emission controller for controlling the first light emitter and the second light emitter to emit the respective light at sampling frequencies different from each other based on a certain relationship between an emission timing of the first light emitter and an emission timing of the second light emitter; a detection controller for controlling the light detector to detect the light from the first light emitter and the light from second light emitter in synchronism with the emission timing of the first light emitter and the emission timing of the second light emitter, respectively; and a storage for storing therein a light detection signal outputted from the light detector as measurement data.

These and other objects, features and advantages of the present invention will become more apparent upon reading the following detailed description along with the accompanying drawing.

DETAILED DESCRIPTION OF THE PREFERRED EMBODIMENTS

Figure 1:
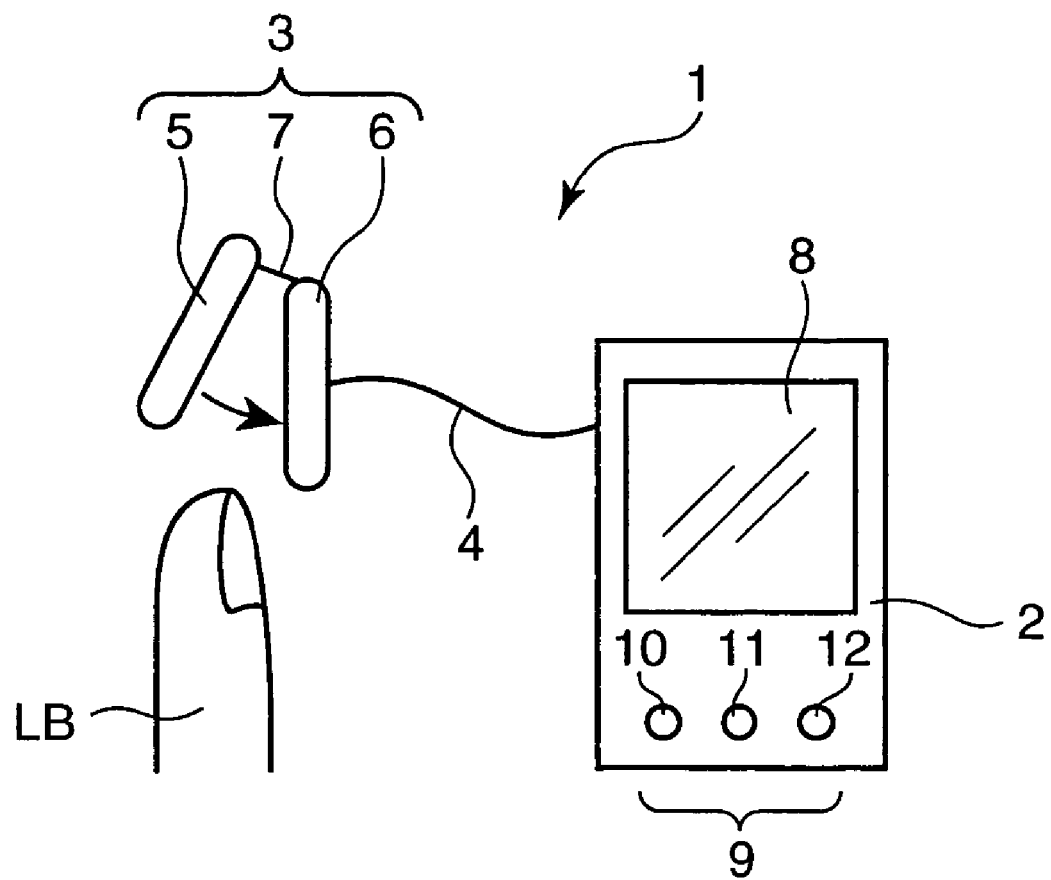
FIG. 1 is a diagram showing an arrangement of a pulse oximeter as an example of a vital information measuring device embodying the invention.
Figure 2:
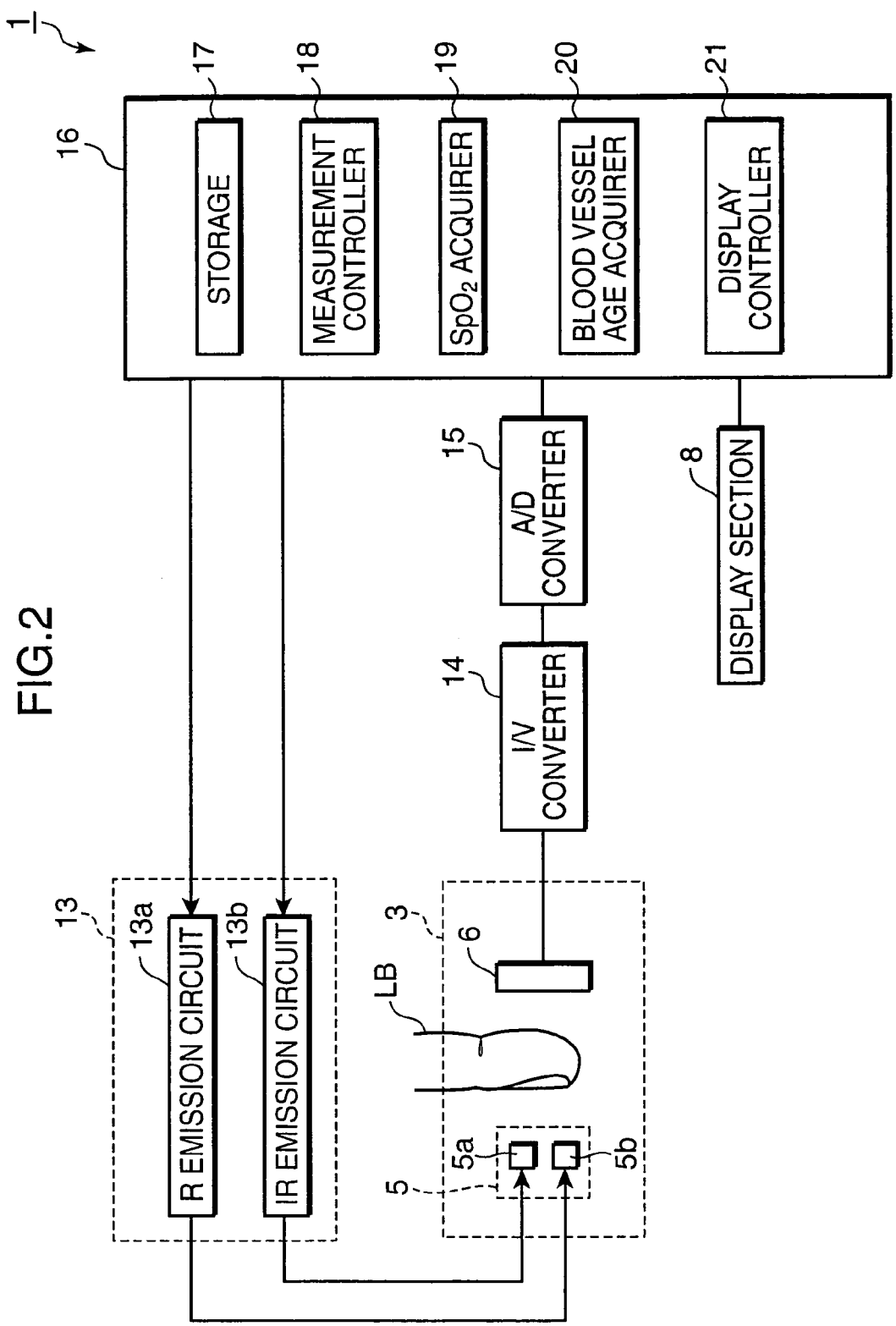
FIG. 2 is a block diagram showing an electrical configuration of the pulse oximeter.

A vital information measuring device as an embodiment of the invention is described referring to the drawings. FIG. 1 is a diagram showing an arrangement of a pulse oximeter, as an example of the vital information measuring device embodying the invention. FIG. 2 is a block diagram showing an electrical configuration of the pulse oximeter 1.

The pulse oximeter 1 in this embodiment is designed to measure vital information through a finger i.e. a fingertip of a subject as a measurement site. As will be described later, the pulse oximeter is enabled to acquire vital information concerning an oxygen saturation in blood of the subject ($SpO_2$, hereinafter, also called as "blood oxygen saturation"), and a blood vessel age representing a degree of arteriosclerosis. In particular, the pulse oximeter 1 is designed to obtain vital information concerning a blood oxygen saturation and a blood vessel age in pair based on measurement data obtained by conducting e.g. an overnight pulse oximetry with the pulse oximeter 1, in place of selectively setting a mode of obtaining information concerning a blood oxygen saturation, and a mode of obtaining information concerning a blood vessel age.

The pulse oximeter 1 includes a rectangular parallelepiped device body 2, and a measuring unit 3 which is electrically connected to the device body 2 by a cable 4. For sake of explanation, the arrangement of the measuring unit 3 is described first.

The measuring unit 3 has a paper-clip like shape capable of securely holding a measurement site e.g. a fingertip of a subject by a biasing force of a spring or a like member. Specifically, the measuring unit 3 has a pair of holding pieces, and a light emitter 5 is provided on one of the holding pieces, and a light detector 6 is provided on the other one of the holding pieces. One ends of the holding pieces are interconnected to each other by a connecting member 7 in such a manner that the other ends thereof are openably closable.

The light emitter 5 is a light source provided with an LED (Light Emitting Diode, hereinafter called as "red LED") 5a for emitting red light R of a wavelength λ1 in a red light region, and an LED (hereinafter, called as "infrared LED") 5b for emitting infrared light IR of a wavelength λ2 in an infrared light region. The red LED 5a and the infrared LED 5b are examples of the first light emitter and the second light emitter in the claimed invention, respectively.

The light detector 6 has a photoelectric conversion device e.g. a silicon photodiode for generating an electric current commensurate with an intensity of received light. In this embodiment, the light detector 6 has a sensitivity at least to the light of the wavelength λ1 and the light of the wavelength λ2. The light detector 6 receives respective light of the wavelengths λ1 and λ2 that have been transmitted through a living tissue LB of the subject. The light detector 6 is an example of the light detector in the claimed invention.

The measuring unit 3 in the embodiment is operated in such a manner that the light emitter 5 alternately emits the red light R of the wavelength λ1 and the infrared light IR of the wavelength λ2, and the light detector 6 performs a light detection in synchronism with the light emission of the light emitter 5, with the fingertip of the subject being securely held by the light emitter 5 and the light detector 6. The light emission of the light emitter 5 and the light detection of the light detector 6 are controlled by a main controller 16 (see FIG. 2) to be described later. The light emission and the light detection with respect to the red light R and the infrared light IR are performed at a predetermined cycle. As will be described later, the embodiment uses specific sampling frequencies concerning emission operations of the red LED 5a and the infrared LED 5b. Upon receiving the light, the light detector 6 outputs a current signal commensurate with the intensity of the received light to an I/V converter 14 (see FIG. 2) provided in the device body 2, which will be described later.

The device body 2 has a display section 8. Examples of the display section 8 are an LCD (Liquid Crystal Display), a 7-segment LED (Light Emitting Diode) display, an organic photoluminescent display, a CRT (Cathode Ray Tube) display, and a plasma display. The display section 8 displays data calculated by the main controller 16 or like information. The display section 8 is an example of the display section in the claimed invention.

The display section 2 includes an operation button group 9 for changing over display contents of the display section 8. The operation button group 9 includes a blood vessel age indication button 10 for setting a first display mode where the blood vessel age is exclusively displayed on the display section 8, out of the information concerning the blood oxygen saturation and the blood vessel age; a blood oxygen saturation indication button 11 for setting a second display mode where the blood oxygen saturation is exclusively displayed on the display section 8, out of the information concerning the blood oxygen saturation and the blood vessel age; and all indication button 12 for setting a third mode where both the blood oxygen saturation and the blood vessel age are displayed on the display section 8. The operation button group 9 is an example of the display mode changer in the claimed invention. An arrangement for allowing a user to enter designation on changeover of the display modes is not limited to the foregoing button arrangement, but various arrangements are applicable.

The device body 2 includes an electric power supply section (not shown) such as a battery or a dry cell which is loaded in an unillustrated loading chamber. The display section 8, various circuits provided in the device body 2, and the measuring unit 3 are driven upon receiving an electric power from the electric power supply section.

As shown in FIG. 2, the pulse oximeter 1 includes the measuring unit 3, the display section 8, an emission controlling section 13, the current-voltage converter 14 (hereinafter, called as the "I/V converter 14"), an analog-to-digital converter 15 (hereinafter, called as the "A/D converter 15"), and the main controller 16.

The measuring unit 3 and the display section 8 shown in FIG. 2 correspond to the measuring unit 3 and the display section 8 shown in FIG. 1, respectively. The emission controlling circuit 13 includes an R emission circuit 13a for driving the red LED 5a to emit red light R of the wavelength λ1 in the red light region, and an IR emission circuit 13b for driving the infrared LED 5b to emit the infrared light IR of the wavelength λ2 in the infrared light region. The emission circuit 13a, 13b has a switching device such as a transistor for changing over the emission operation of the red LED 5a, the infrared LED 5b, a transistor such as an n-MOS FET transistor for supplying a current to the red LED 5a, the infrared LED 5b in accordance with a switching operation of the switching device, and a resistive device.

The I/V converter 14 converts a current signal outputted from the light detector 6 at a predetermined cycle into a voltage signal to output the voltage signal to the A/D converter 15 as an analog photoelectric pulse wave signal. The A/D converter 15 converts the analog photoelectric pulse wave signal outputted from the I/V converter 14 into a digital photoelectric pulse wave signal to output the digital photoelectric pulse wave signal to the main controller 16.

The main controller 16 includes a microprocessor or a DSP (Digital Signal Processor), and detects an arterial oxygen saturation and/or a blood vessel age based on the inputted signal in accordance with a program or data stored in an ROM serving as a storage 17.

Examples of the storage 17 are an SRAM, a DRAM, an EEPROM, and a flash memory. The storage 17 stores data calculated by the main controller 16 including measurement data to be described later. The storage 17 is an example of the storage in the claimed invention. Alternatively, an external storage may be connected to the pulse oximeter 1 to record measurement data or an analysis result, in place of the storage 17.

The main controller 16 functionally includes a measurement controller 18, an $SpO_2$ acquirer 19, a blood vessel age acquirer 20, and a display controller 21 to obtain the information concerning the blood oxygen saturation and the blood vessel age in pair, as described above, and to change over the display mode concerning the obtained information among the first, the second, and the third display modes.

Figure 3:
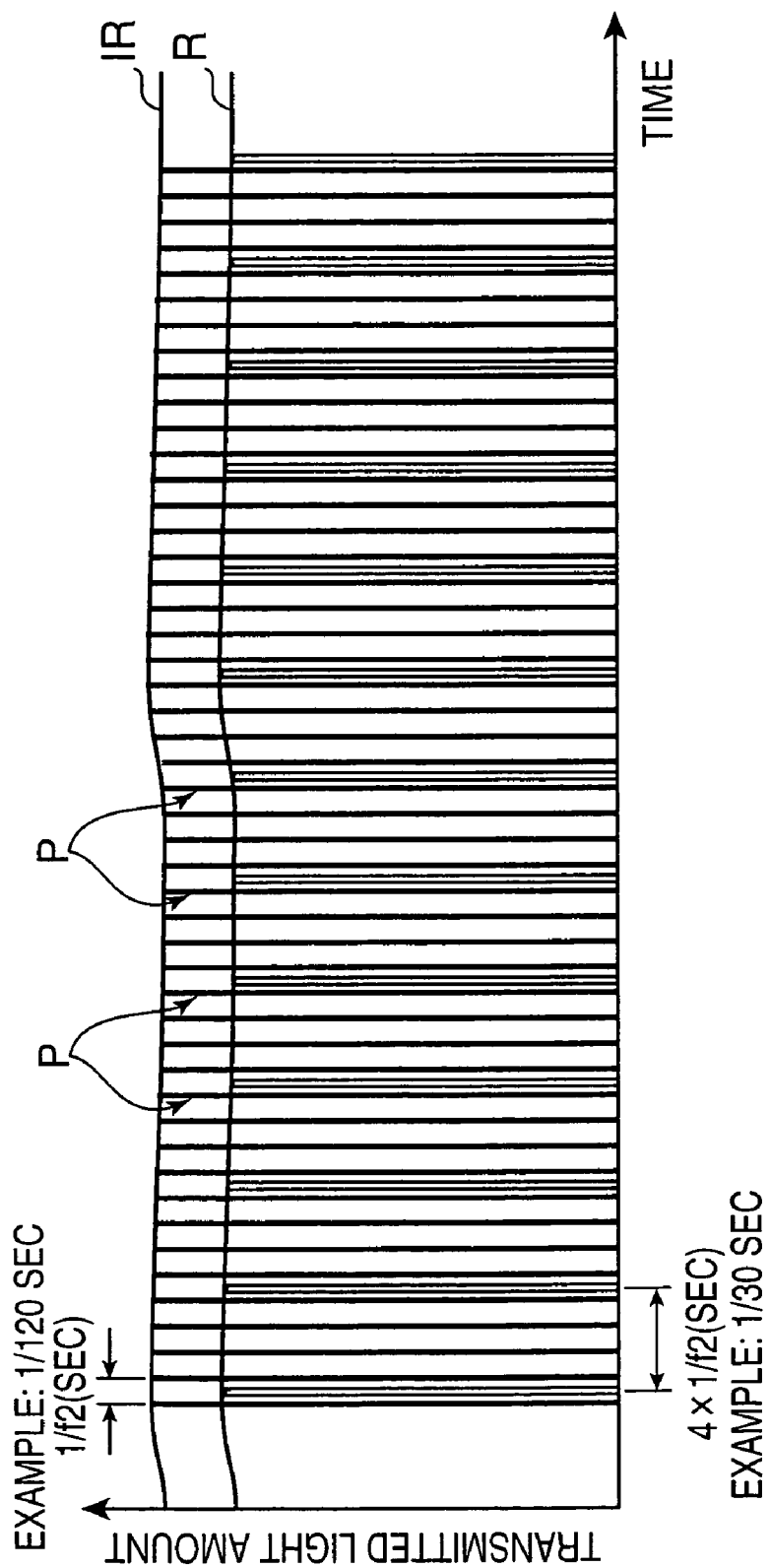
FIG. 3 is a graph showing emission operations of LEDs.

The measurement controller 18 controls the emission operations of the red LED 5a and the infrared LED 5b. FIG. 3 is a graph showing emission operations of the red LED 5a and the infrared LED 5b. As shown in FIG. 3, upon receiving a measurement start command signal through manipulation of the pulse oximeter 1 by the user, the measurement controller 18 controls the red LED 5a to emit red light R at a sampling frequency f1 e.g. 30 Hz, and controls the infrared LED 5b to emit infrared light IR at a sampling frequency f2 e.g. 120 Hz, which is higher than the sampling frequency of the red LED 5a. The reason for differentiating the sampling frequencies between the red LED 5a and the infrared LED 5b will be described later. 30 Hz and 120 Hz are examples of the sampling frequencies of the red LED 5a and the infrared LED 5b. The sampling frequencies to be used in the embodiment are not limited to the aforementioned values.

The measurement controller 18 controls the emission operation of the infrared LED 5b by setting the sampling frequency f2 of the infrared LED 5b to an integral multiplication of the sampling frequency f1, in other words, by setting f2=m×f1 where m is an integer. FIG. 3 shows an arrangement, in which the sampling frequency f2 of the infrared LED 5b is set four times as large as the sampling frequency f1 of the red LED 5a, in other words, an emission operation of the infrared LED 5b is conducted at ¼ cycle, as compared with an emission operation of the red LED 5a. The reason for setting the sampling frequency f2 of the infrared LED 5b to an integral multiplication of the sampling frequency f1 of the red LED 5a will also be described later.

The light detector 6 is incapable of discriminating red light R to be emitted from the red LED 5a from infrared light IR to be emitted from the infrared LED 5b if emission timings of the red LED 5a and the infrared LED 5b are coincident to each other. In order to avoid the drawback, the measurement controller 18 controls the red LED 5a and the infrared LED 5b to emit the respective light with phases displaced from each other. For instance, the emission timing of the red LED 5a may be set in the middle of two consecutive emission timings of the infrared LED 5b.

The measurement controller 18 controls the red LED 5a and the infrared LED 5b to perform the above emission operations, and also controls the light detector 6 to detect the respective light from the red LED 5a and the infrared LED 5b in synchronism with the emission operations of the red LED 5a and the infrared LED 5b. Each time a light detection signal is outputted from the light detector 6, the measurement controller 18 sequentially stores the light detection signal after A/D conversion into the storage 17 as measurement data. The measurement controller 18 corresponds to the emission controller and the detection controller in the claimed invention.

The $SpO_2$ acquirer 19 acquires i.e. analyzes information concerning a blood oxygen saturation i.e. $SpO_2$ data of the subject, using the measurement data stored in the storage 17. Oxygen is transported by oxidation/reduction of hemoglobin in the blood. The hemoglobin has such optical characteristics that absorption of red light is decreased, and absorption of infrared light is increased when the hemoglobin is oxidized, and, conversely, absorption of red light is increased and absorption of infrared light is decreased when the hemoglobin is reduced. The $SpO_2$ acquirer 19 obtains $SpO_2$ data by measuring a change in transmitted light amounts of the red light and the infrared light, which are detected by the light detector 6, by utilizing the optical characteristics. The obtained $SpO_2$ data is sequentially stored in the storage 17.

Now, a principle as to how the $SpO_2$ acquirer 19 calculates the blood oxygen saturation using light is described.

Oxygen is transported to cells of a living body by way of hemoglobin (Hb) in blood. Hemoglobin (Hb) turns into oxidized hemoglobin ($HbO_2$) by bonding to oxygen in lungs, and the oxidized hemoglobin turns into hemoglobin again by consumption of the oxygen in the cells of the living body. The blood oxygen saturation i.e. $SpO_2$ represents a ratio of oxidized hemoglobin in blood, and is expressed by the following formula (1) where CHb is a concentration of hemoglobin, and $CHbO_2$ is a concentration of oxidized hemoglobin.

$$SpO_2\ (\%) = \frac{CHbO_2}{CHb + CHbO_2} \times 100 \qquad (1)$$

Figure 4:
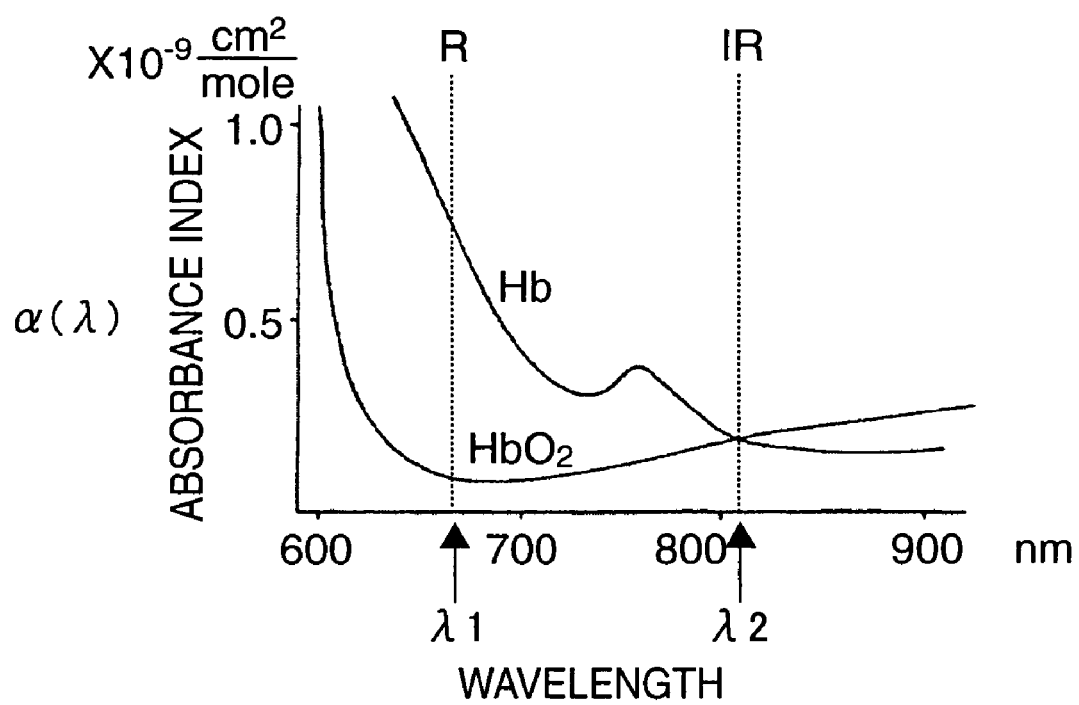
FIG. 4 is a graph showing light absorption characteristics of hemoglobin and oxidized hemoglobin.

Absorbances of hemoglobin and oxidized hemoglobin are wavelength dependent. Absorbance indexes $\alpha(\lambda)$ of hemoglobin and oxidized hemoglobin have light absorption characteristics as shown in FIG. 4. The axis of abscissas in FIG. 4 represents a wavelength of light (unit: nm), and the axis of ordinate in FIG. 4 represents an absorbance index (unit: $10^{-9}$ $cm^2$/mole).

As shown in FIG. 4, hemoglobin and oxidized hemoglobin have different light absorption characteristics. Hemoglobin absorbs more light than oxidized hemoglobin with respect to the red light R of the wavelength $\lambda 1$ in the red light region, but absorbs less light than the oxidized hemoglobin with respect to the infrared light IR of the wavelength $\lambda 2$ in the infrared light region, which is out of the red light region. Specifically, for instance, assuming that the wavelength of the red light R is 660 nm where a difference in absorbance index between oxidized hemoglobin and hemoglobin is the largest, and the wavelength of the infrared light IR is 815 nm where absorbance indexes of oxidized hemoglobin and hemoglobin are identical to each other, the transmitted light amount of the infrared light IR does not change even if a ratio in amount of the oxidized hemoglobin versus the hemoglobin is changed. On the other hand, an increased amount of the hemoglobin decreases the transmitted light amount of the red light R, and an increased amount of the oxidized hemoglobin increases the transmitted light amount of the red light R. In other words, calculating a ratio of transmitted light amounts of the red light R versus the infrared light IR enables to obtain a blood oxygen saturation.

As mentioned above, the pulse oximeter 1 obtains the information concerning the blood oxygen saturation by utilizing a difference in light absorption characteristics between hemoglobin and oxidized hemoglobin with respect to the red light R and the infrared light IR. It should be noted that a pulse rate can be obtained by utilizing a pulse waveform.

Figure 5A:
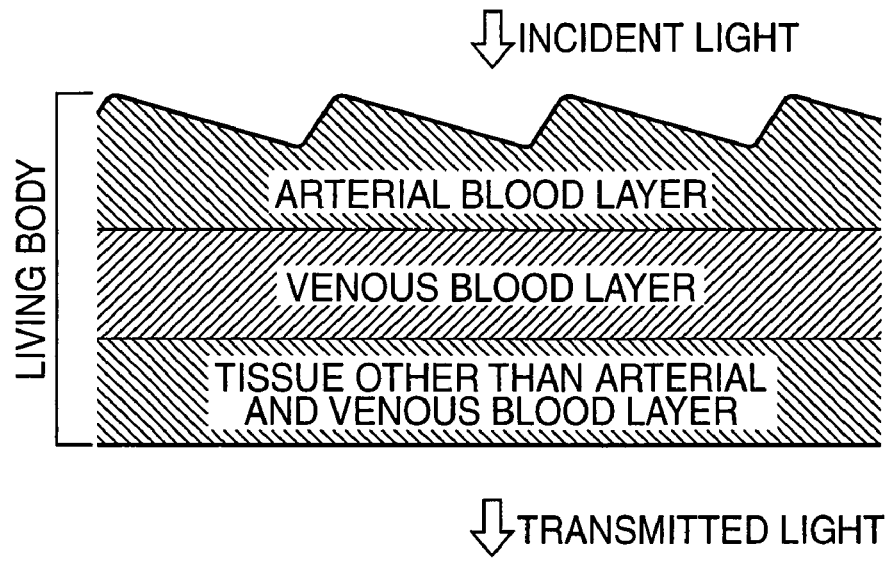
FIGS. 5A and 5B are diagrams for explaining light absorption with respect to a living body.

When light is irradiated onto a living body, a part of the light is absorbed into the living body, and the rest of the light is transmitted through the living body. The living body includes an arterial blood layer, a venous blood layer, and a tissue other than the arterial blood layer and the venous blood layer. As shown in FIG. 5A, light absorption in the living body includes absorption by the tissue other than the arterial blood layer and the venous blood layer, absorption by the venous blood layer, and absorption by the arterial blood layer. Since the tissue other than the arterial blood layer and the venous blood layer, and the venous blood layer do not change with time, the absorptions by these sites are substantially constant.

Figure 5B:
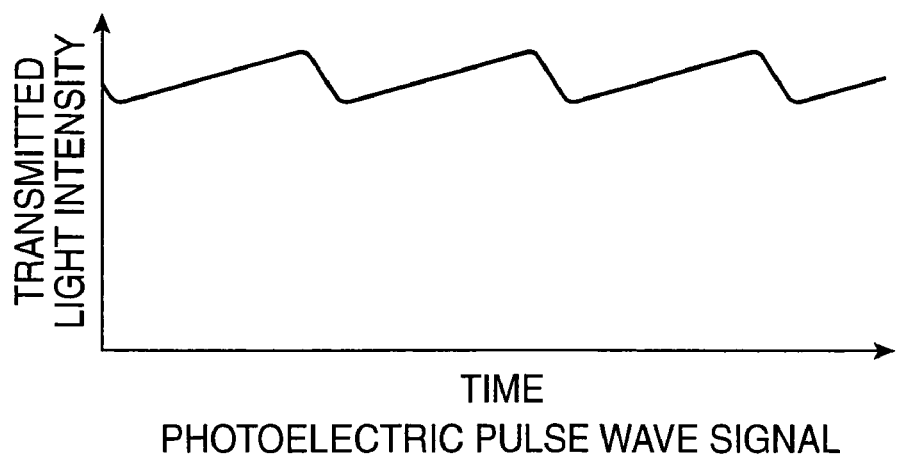

On the other hand, the arterial blood layer changes its diameter by a heartbeat. Since the diameter of the arterial blood layer is changed by the heartbeat, the light absorption by the arterial blood layer is changed with time by the heartbeat, as shown in FIG. 5B. In other words, it is conceived that a change in transmitted light intensity solely reflects a behavior of the arterial blood layer, and hardly includes an influence of the tissue other than the arterial blood layer and the venous blood layer, and an influence of the venous blood layer. Referring to FIG. 5B, the axis of abscissa represents a time, and the axis of ordinate represents a transmitted light intensity.

Figure 6A:
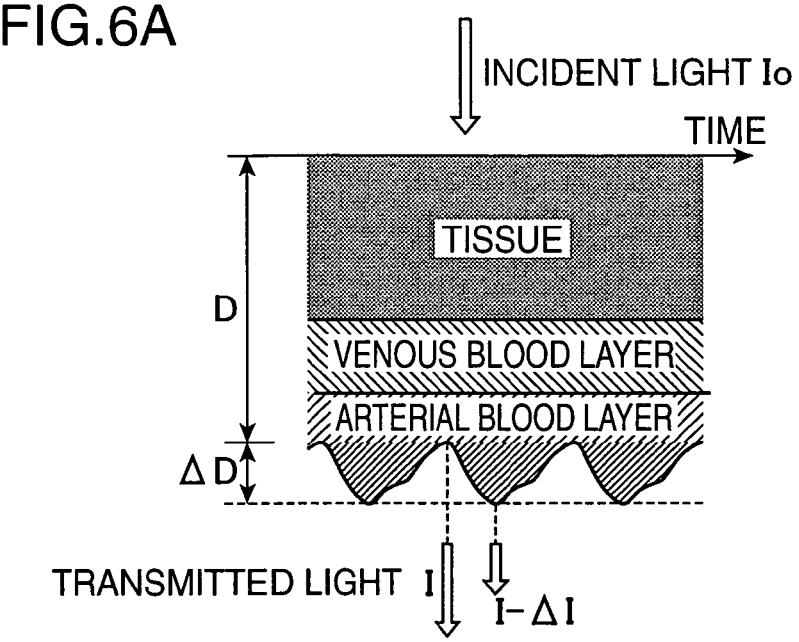
FIGS. 6A through 6C are diagrams schematically showing a relationship between incident light and transmitted light with respect to a living body.

In comparing a change in light amount between the red light R and the infrared light IR, it is necessary to cancel a difference in incident light amount between the red light R and the infrared light IR. FIG. 6A is a diagram schematically showing a relationship between light that is incident onto a living body, and light that is transmitted through the living body.

It is substantially difficult to make the incident light amount I0 onto the living body identical to each other between the red light R and the infrared light IR. Even if the incident light amount I0 is made identical between the red light R and the infrared light IR, it is impossible to compare solely a change in transmitted light intensity through the arterial blood layer between the red light R and the infrared light IR, because absorptive powers of the tissue other than the arterial blood layer and the venous blood layer, and of the venous blood layer are different between the red light R and the infrared light IR.

Figure 6B:
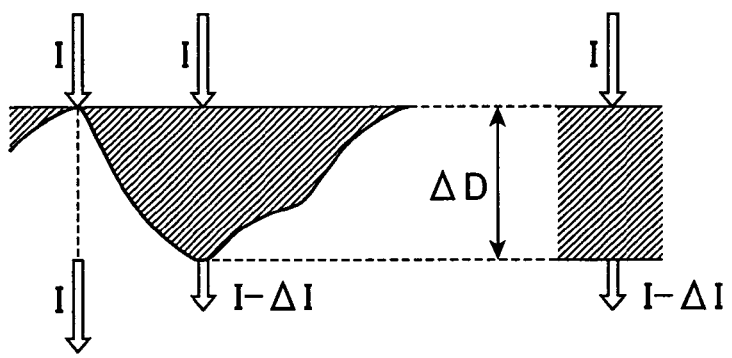
Figure 6C:
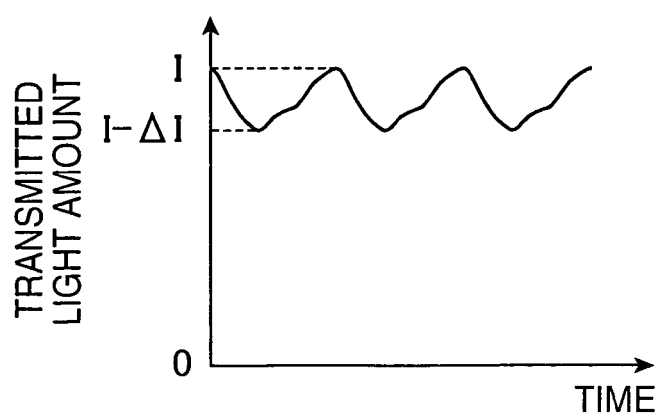

In view of the above, as shown in FIG. 6A, let it be assumed that a transmitted light amount through an arterial blood portion with a possible smallest diameter i.e. a possible largest transmitted light amount is defined as "I", and a transmitted light amount through an arterial blood portion with a possible largest diameter i.e. a possible smallest transmitted light amount is defined as (I−ΔI). Then, as shown in FIGS. 6B and 6C, transmitted light with the light amount (I−ΔI) is supposed to be obtained if light with the light amount "I" is irradiated onto an arterial blood layer with a thickness ΔD.

Figure 7:
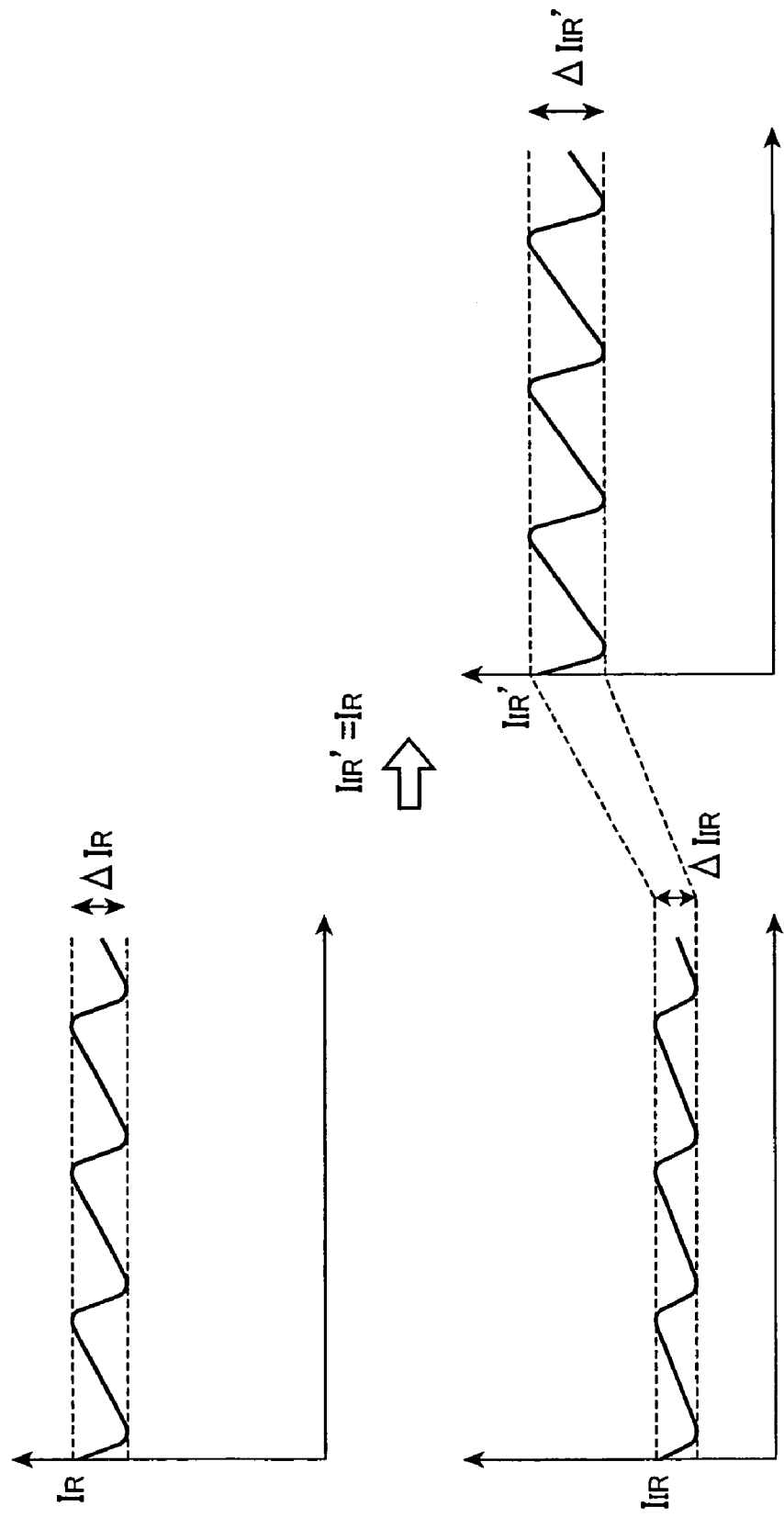
FIG. 7 is a diagram for explaining normalization of a transmitted light amount of infrared light.

Then, as shown in FIG. 7, normalization is conducted to make a transmitted light amount $I_R$ of the red light R coincident with a transmitted light amount $I_{IR}$ of the infrared light IR. Specifically, by conducting normalization to satisfy an equation: $I_{IR}'=I_R$ where $I_{IR}'$ corresponds to the transmitted light amount $I_{IR}$, a ratio of a change in light amount with respect to the arterial blood layer between the red light R and the infrared light IR is calculated, i.e. an equation: $(\Delta I_R/I_R)/(\Delta I_{IR}/I_{IR})$ is implemented, whereby a blood oxygen saturation is calculated.

A relationship of incident light versus reflected light can be expressed by the following formula (2) according to the Lambert Beer rule.

$$\log\left(\frac{I}{I-\Delta I}\right) = EC\Delta D \qquad (2)$$

where E is an absorbance index of an absorptive object, and C is a concentration of the absorptive object.

Substituting the wavelengths of the red light R and the infrared light IR in the formula (2), respectively, specifically, substituting $I_R$ and $I_{IR}$ for I in the formula (2), respectively, and obtaining a ratio of the resultant two formulae enables to yield the following formula (3).

$$\frac{\log\{I_R/(I_R-\Delta I_R)\}}{\log\{I_{IR}/(I_{IR}-\Delta I_{IR})\}} = \frac{E_R C\Delta D}{E_{IR} C\Delta D} = \frac{E_R}{E_{IR}} \qquad (3)$$

where $I_R$ is a transmitted light amount of red light R, $I_{IR}$ is a transmitted light amount of infrared light IR, $E_R$ is an absorbance index of red light R, and $E_{IR}$ is an absorbance index of infrared light IR.

Figure 8:
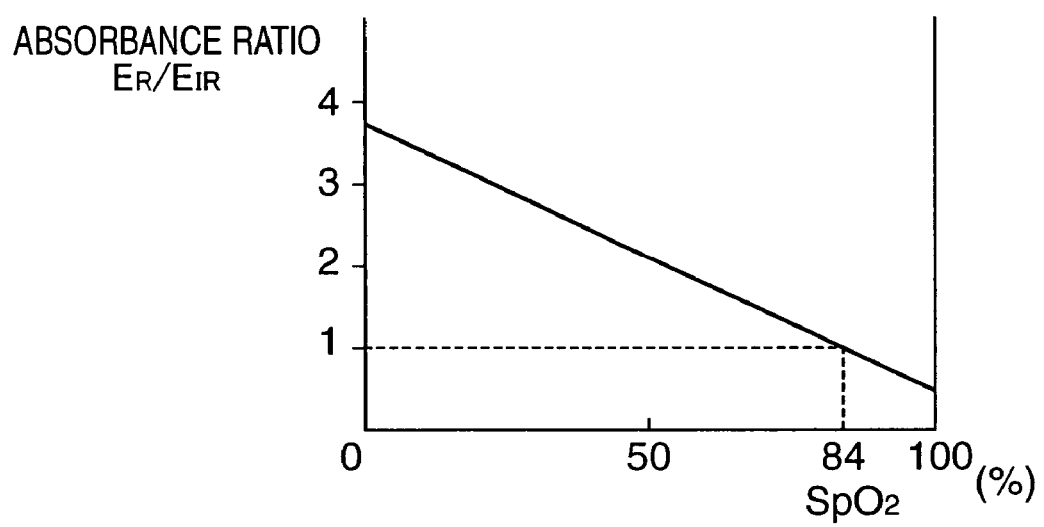
FIG. 8 is a graph showing a relationship between an absorbance ratio and a blood oxygen saturation.

FIG. 8 is a graph showing a relationship between an absorbance ratio ($E_R/E_{IR}$), and a blood oxygen saturation i.e. SpO$_2$ in the case where the wavelengths of the red light R and the infrared light IR are 660 nm and 815 nm, respectively. As shown in FIG. 8, the blood oxygen saturation i.e. SpO$_2$ is increased in proportion to lowering of the absorbance ratio ($E_R/E_{IR}$).

The SpO$_2$ acquirer 19 acquires the SpO$_2$ data, using the measurement data obtained based on both of the output light from the red LED 5a and the output light from the infrared LED 5b. In this embodiment, as mentioned above, the red LED 5a and the infrared LED 5b are controlled to emit the respective light with the sampling frequencies different from each other. Accordingly, the numbers of measurement data obtained from the respective light are different from each other.

The sampling frequency f1 of the red LED 5a is set to such a value that enables to acquire SpO$_2$ data having required precision, considering the number of measurement data, and balance between a storage capacity of the storage 17 for storing the measurement data, and required acquisition precision on SpO$_2$ data. Consequently, the number of measurement data obtained based on the output light from the infrared LED 5b is excessively large in acquiring the information concerning the blood oxygen saturation i.e. the SpO$_2$ data.

In view of the above, in this embodiment, the SpO$_2$ acquirer 19 limitedly uses the measurement data used in acquiring the SpO$_2$ data, out of the measurement data obtained based on the output light from the infrared LED 5b so that the SpO$_2$ data is acquired using the limitedly obtained measurement data and measurement data obtained based on the output light from the red LED 5a.

As mentioned above, since the sampling frequency f2 of the infrared LED 5b is set to an integral multiplication of the sampling frequency f1 of the red LED 5a i.e. f2=m×f1, measurement data to be used can be easily restricted.

More specifically, if the sampling frequency f2 of the infrared LED 5b is not an integral multiplication of the sampling frequency f1 of the red LED 5a, measurement data at a predetermined time interval i.e. a cycle corresponding to the sampling frequency of the red LED 5a cannot be obtained, as far as measurement data based on the output light from the infrared LED 5b is concerned. Accordingly, in this case, data interpolation using the measurement data obtained based on the output light from the infrared LED 5b is required to obtain a number of rows of measurement data which are aligned every predetermined time interval corresponding to the sampling frequency of the red LED 5a.

On the other hand, in this embodiment, measurement data at every predetermined time interval corresponding to the sampling frequency of the red LED 5a is obtained by setting the sampling frequency f2 of the infrared LED 5b to an integral multiplication of the sampling frequency f1 of the red LED 5a. This eliminates a data interpolation, as required in the above case, and enables to limitedly use the measurement data merely by extracting the measurement data at every predetermined time interval corresponding to the sampling frequency of the red LED 5a. This enables to simplify the measurement data limitation process, as compared with a case where the sampling frequency f2 of the infrared LED 5b is not equal to an integral multiplication of the sampling frequency f1 of the red LED 5a. Consequently, designing a program for functioning the main controller 16 as the $SpO_2$ acquirer 19 is made easy.

The $SpO_2$ acquirer 19 obtains the same number of measurement data as the measurement data obtained based on the output light from the red LED 5a by the above extraction operation, and acquires information concerning a blood oxygen saturation based on the extracted measurement data.

For instance, as shown by the arrows P in FIG. 3, the $SpO_2$ acquirer 19 extracts measurement data obtained based on the output light from the infrared LED 5b immediately before an output operation of the red LED 5a, out of the measurement data obtained based on the output light from the infrared LED 5b, and acquires $SpO_2$ data, using the extracted measurement data and measurement data obtained based on the output light from the red LED 5a. The $SpO_2$ acquirer 19 is an example of the second analyzer in the claimed invention.

The blood vessel age acquirer 20 acquires i.e. analyzes information concerning a blood vessel age i.e. an arteriosclerosis index representing an arteriosclerosis degree of an artery, using the measurement data stored in the storage 17. The acquired blood vessel age information is sequentially stored in the storage 17.

Figure 9:
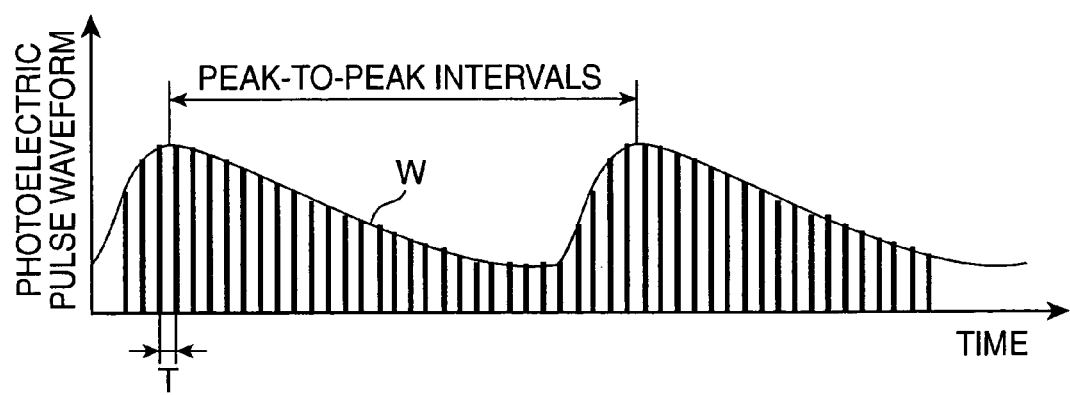
FIG. 9 is a graph showing a photoelectric pulse waveform measured at a cycle T.

FIG. 9 is a graph showing a photoelectric pulse waveform W measured at a cycle T. The photoelectric pulse waveform W is obtained by performing a moving averaging process with respect to an instantaneous photoelectric pulse wave value detected at the cycle T along a time axis. The blood vessel age is estimated by a derivation of the photoelectric pulse waveform W. Specifically, an acceleration pulse waveform can be obtained by a second order derivation of the photoelectric pulse waveform W as shown in FIG. 9. The blood vessel age can be estimated by extracting a characteristic on the acceleration pulse waveform. There is also known an approach of estimating a blood vessel age based on a pulse waveform.

Figure 10A:
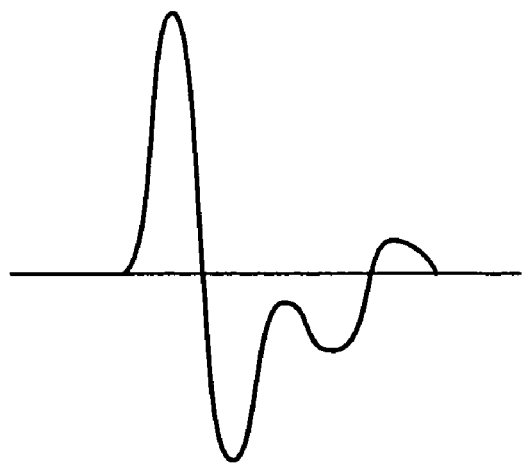
FIGS. 10A and 10B are graphs showing examples of an acceleration pulse waveform obtained by a second order derivation of the photoelectric pulse waveform shown in FIG. 9.
Figure 10B:
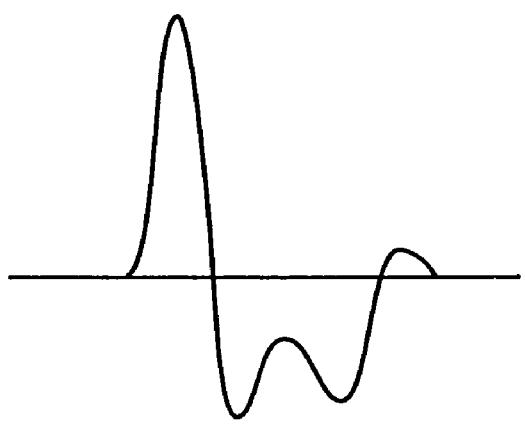

FIGS. 10A and 10B are graphs showing an example of the acceleration pulse waveform. FIG. 10A shows an acceleration pulse waveform typically obtained from a normal healthy person in thirties, and FIG. 10B shows an acceleration pulse waveform typically obtained from a normal healthy person in sixties. Characteristics on the acceleration pulse waveform differ depending on ages, which conceivably results from a change in blood vessel resilience, i.e., a resilience force of a blood vessel. In view of this, an estimate value of the blood vessel age can be obtained by: preparing typical acceleration pulse waveform patterns depending on generations in advance; and by assessing a similarity between the typical acceleration pulse waveform patterns and the obtained acceleration pulse waveform.

An estimate diagnosis on the blood vessel age requires a process of a second order derivation of a photoelectric pulse waveform. Accordingly, if an original photoelectric pulse waveform lacks fineness, an acceleration pulse waveform which accurately reflects a blood vessel resilience of a subject is hardly obtainable. In view of this, it is appropriate to set the cycle T to a relatively short cycle in the estimate diagnosis on the blood vessel age.

In view of the above, the blood vessel age acquirer 20 generates the photoelectric pulse waveform as shown in FIG. 9 by performing a data alignment process of developing the measurement data obtained based on the output light from the infrared LED 5b having a relatively high sampling frequency, out of the measurement data stored in the storage 17 using the measurement controller 18 along a time axis, and acquires an acceleration pulse waveform by a second order derivation of the generated photoelectric pulse waveform. Then, the blood vessel age acquirer 20 acquires an estimate assessment score of the blood vessel age by: comparing the acquired acceleration pulse waveform with the prepared generations-based typical acceleration pulse waveform patterns; and assessing a similarity between the acquired acceleration pulse waveform and the prepared typical acceleration pulse waveform patterns.

Figure 11:
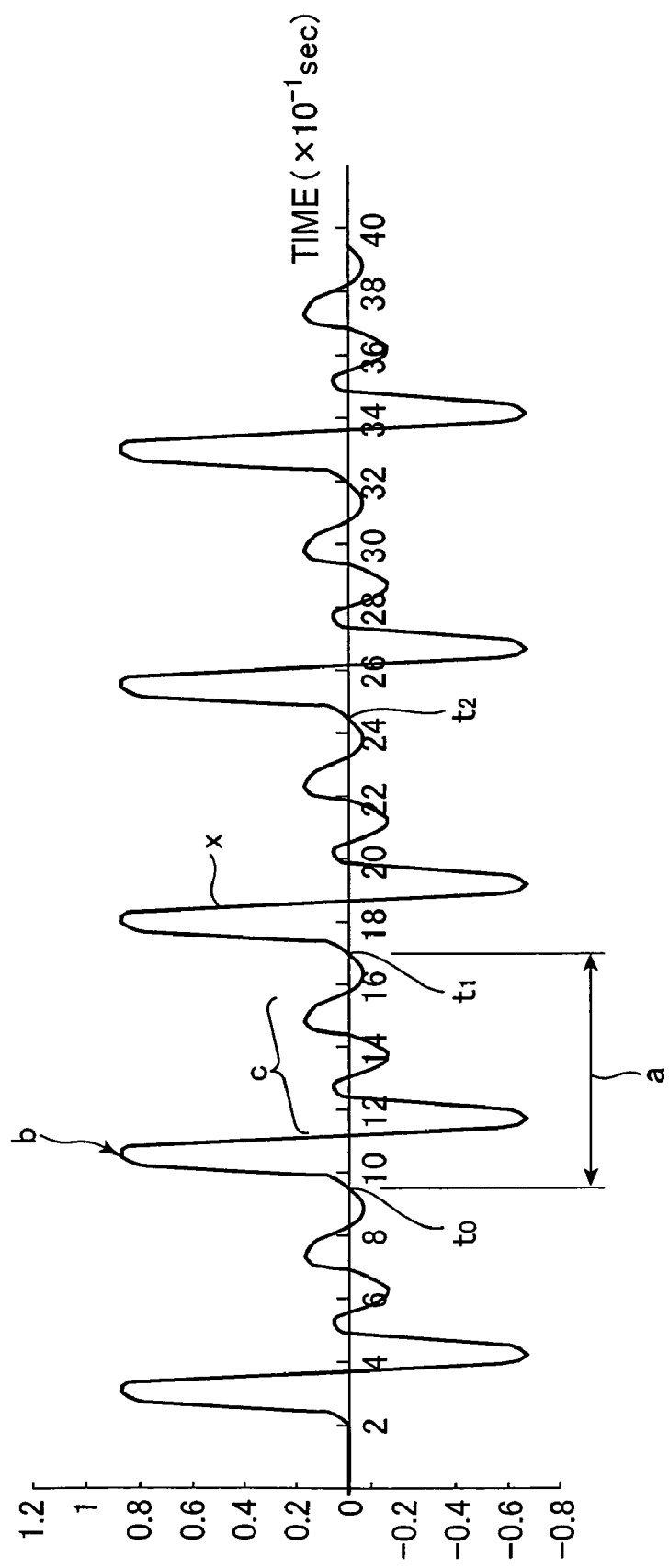
FIG. 11 is a graph showing an example of an acceleration pulse waveform obtained by a second order derivation of a photoelectric pulse waveform.

FIG. 11 is a graph showing an example of an acceleration pulse waveform X obtained by a second order derivation of a photoelectric pulse waveform. In the acceleration pulse waveform X, a pulse wave component in a time zone indicated by the symbol "a" corresponds to a pulse wave component within one heartbeat. The pulse wave component within the one heartbeat includes a large variation in waveform indicated by the symbol "b", followed by a group of small variations in waveform indicated by the symbol "c". The pulse wave component having the above pattern is cyclically repeated to constitute the acceleration pulse waveform X.

Figure 12:
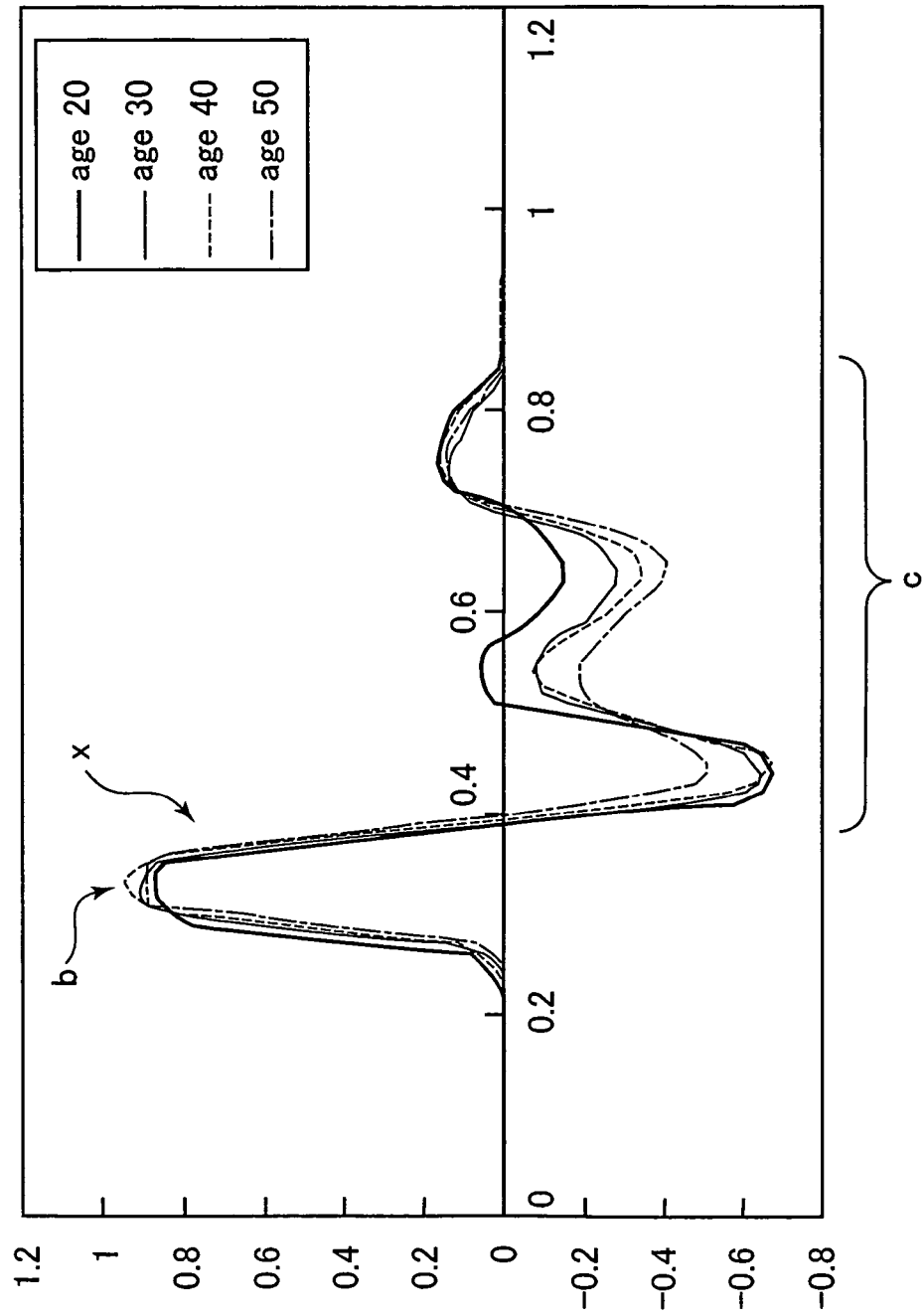
FIG. 12 is a graph showing typical generations-based characteristics on pulse waveform components of an acceleration pulse waveform per pulsation, indicated by the symbol "a" in FIG. 11.

The acceleration pulse waveform X is known to be varied or differ depending on the ages i.e. generations. FIG. 12 is a graph showing typical acceleration pulse waveform patterns based on the generations with respect to the pulse waveform component per heartbeat indicated by the symbol "a" in FIG. 11. As is obvious from FIG. 12, different characteristics are observed among twenties, thirties, forties, and fifties concerning the group of small variations in waveform indicated by the symbol "c", which follows the large variation in waveform indicated by the symbol "b". Conceivably, aging results in hardening of the arteries and lowering of a blood vessel resilience, with the result that a response to the pulse wave component indicated by the symbol "b" is delayed, thus causing the differences in the waveform component indicated by the symbol "c".

Based on the above finding, the blood vessel age acquirer 20 estimates i.e. analyzes the blood vessel age of the subject, and controls the display section 8 to display an analysis result as an indication "43 years old", or "thirties", or as a message "YOUR BLOOD VESSEL AGE IS 45 years old." Alternatively, a characteristic coefficient representing a characteristic on the acceleration pulse waveform may be displayed/stored. The blood vessel age acquirer 20 is an example of the first analyzer in the claimed invention.

As mentioned above, it is required to output two kinds of light having wavelengths different from each other with a relatively low sampling frequency, respectively so as to acquire SpO$_2$ data i.e. information concerning a blood oxygen saturation. On the other hand, it is required to output light of a single wavelength with a relatively high sampling frequency so as to acquire information concerning a blood vessel age.

In view of the above, in this embodiment, the red LED 5a is controlled to emit light with the sampling frequency f1, and the infrared LED 5b is controlled to emit light with the sampling frequency f2 (>f1) so as to obtain information concerning a blood oxygen saturation i.e. SpO$_2$ and a blood vessel age in pair based on the measurement data obtained by a measuring operation. Also, substantially all the measurement data obtained based on the output light from the red LED 5a, and the measurement data extracted at every predetermined time interval i.e. at every predetermined cycle corresponding to the sampling frequency f1 of the red LED 5a out of the measurement data obtained based on the output light from the infrared LED 5b are used to acquire the information concerning the blood oxygen saturation i.e. the SpO$_2$ data, and substantially all the measurement data obtained based on the output light from the infrared LED 5b are used to acquire the information concerning the blood vessel age.

The display controller 21 controls the display section 8 to display an analysis result in response to the user's manipulation of a corresponding button of the operation button group 9. Specifically, in response to a depressing operation of the blood vessel age indication button 10, the display controller 21 sets the display mode of the pulse oximeter 1 to the first display mode so that the display section 8 exclusively displays the blood vessel age out of the information concerning the blood oxygen saturation and the blood vessel age. In response to a depressing operation of the oxygen saturation indication button 11, the display controller 21 sets the display mode of the pulse oximeter 1 to the second display mode so that the display section 8 exclusively displays the blood oxygen saturation out of the information concerning the blood oxygen saturation and the blood vessel age. In response to a depressing operation of the all indication button 12, the display controller 21 sets the display mode of the pulse oximeter 1 to the third display mode so that the display section 8 displays both the blood oxygen saturation and the blood vessel age. The controller 21 corresponds to the display mode changer in the claimed invention.

Figure 13:
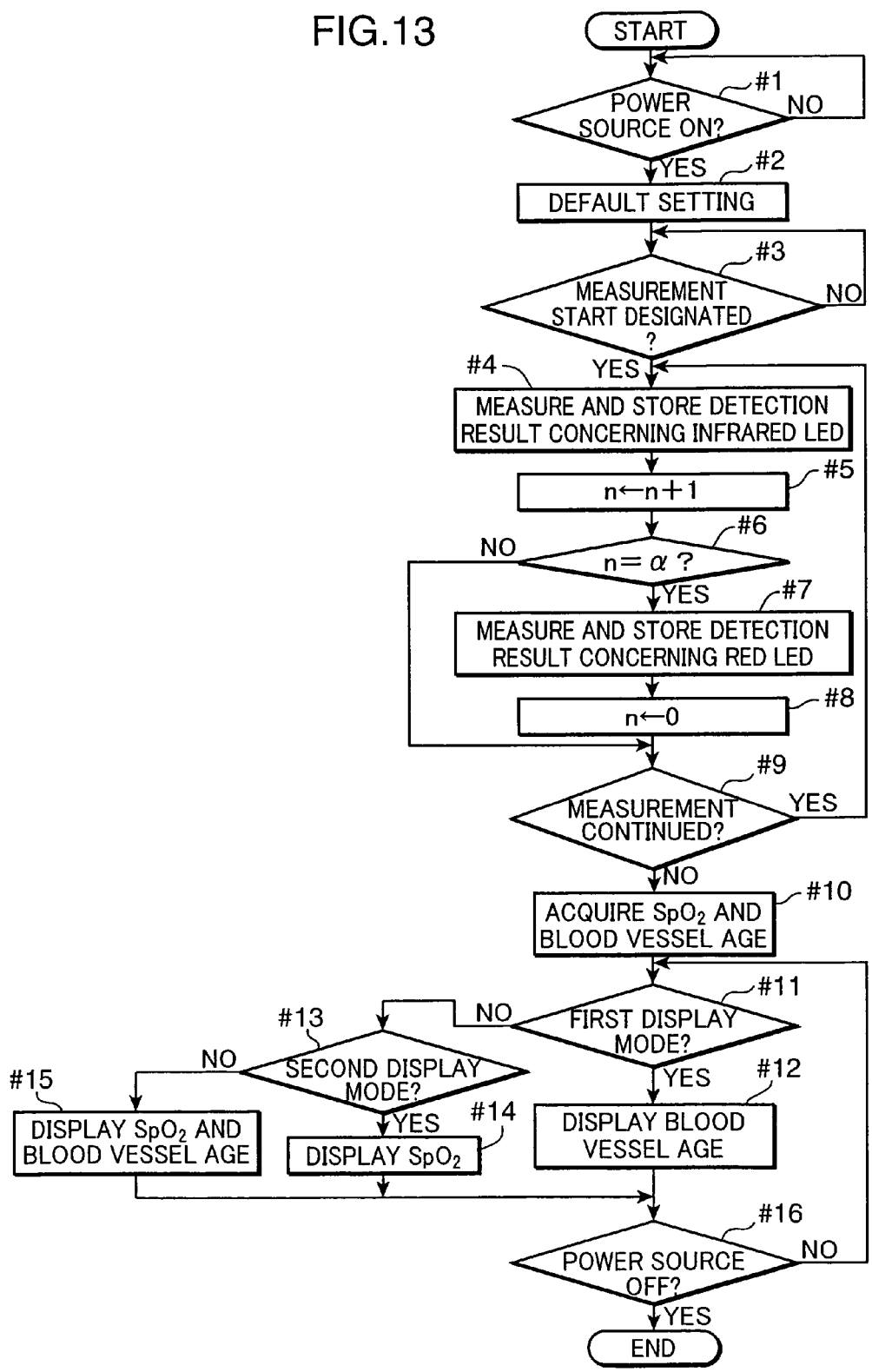
FIG. 13 is a flowchart showing a measurement operation to be executed by the pulse oximeter.
Figure 14:
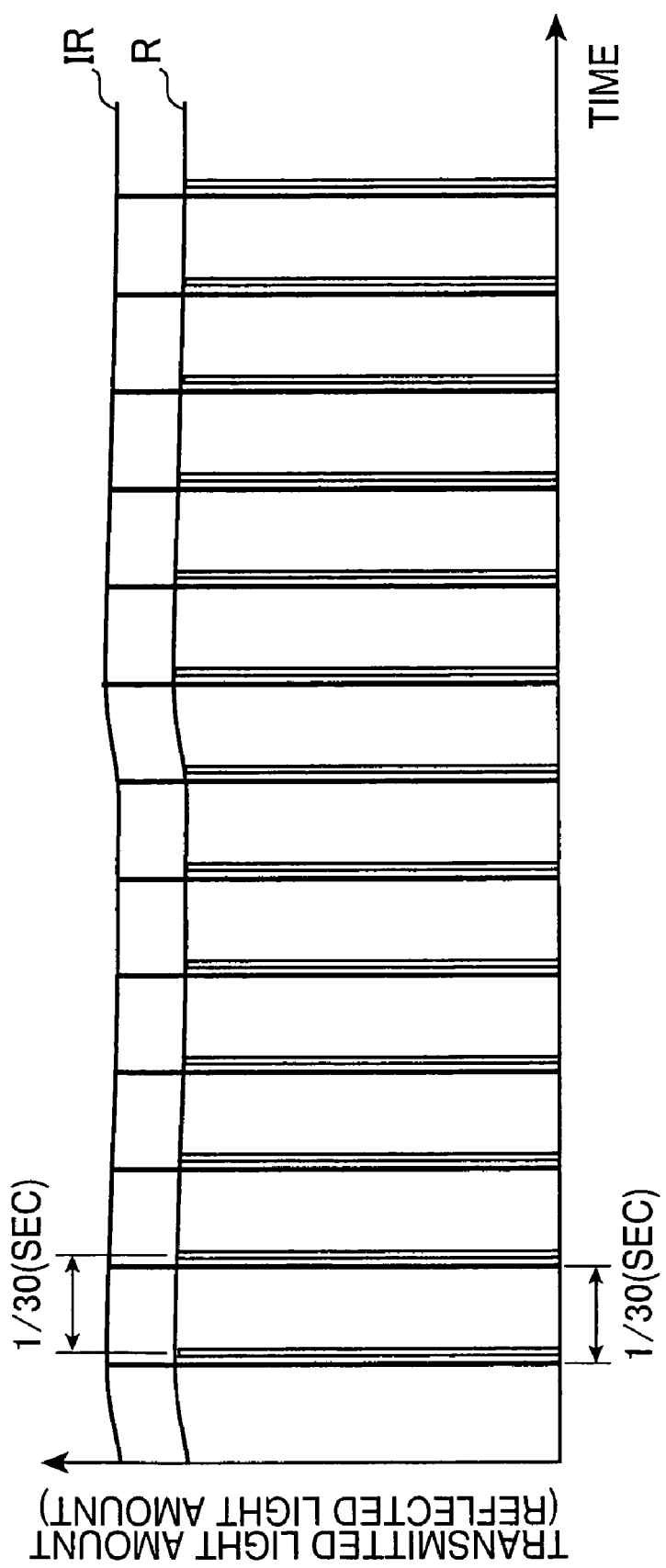
FIG. 14 is a graph showing a conventional approach of measuring a blood oxygen saturation.
Figure 15:
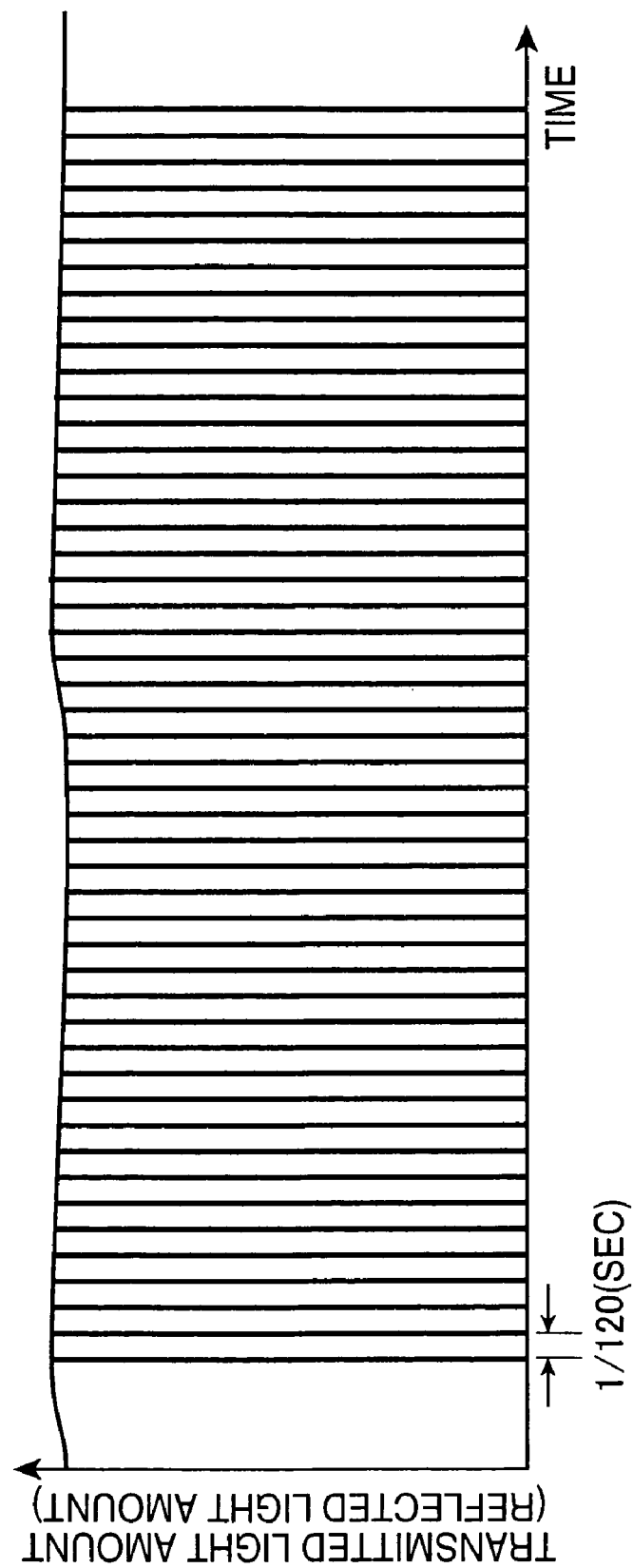
FIG. 15 is a graph showing a conventional approach of measuring a blood vessel age.

FIG. 13 is a flowchart showing a measuring operation to be executed by the pulse oximeter 1 in the embodiment.

Referring to FIG. 13, when a main power source (not shown) is turned on in response to the user's manipulation of an unillustrated power source button (Step #1), the main controller 16 executes various default settings (Step #2). The main controller 16 has a counter (not shown) for counting the number of times of emissions of the infrared LED 5b. The default settings to be executed by the main controller 16 include resetting the count value of the counter to an initial value, and setting the sampling frequencies of the red LED 5a and the infrared LED 5b to f1 and f2, respectively.

Subsequently, when a measurement start is designated by issuance of an unillustrated measurement start command signal (YES in Step #3), the main controller 16 controls the infrared LED 5b to emit light and controls the light detector 6 to detect the light, and stores a light detection signal obtained from the light detector 6 into the storage 17 as measurement data (Step #4). Then, the main controller 16 increments the count value of the counter by one (Step #5).

Then, the main controller 16 judges whether the count value of the counter has reached a predetermined value "α" (in the above example, α=4) (Step #6). If it is judged that the count value has not reached the predetermined value "α" (NO in Step #6), the routine proceeds to Step #9. If, on the other hand, it is judged that the count value has reached the predetermined value "α" (YES in Step #6), the main controller 16 controls the red LED 5a to emit light, controls the light detector 6 to detect the light, stores a light detection signal obtained from the light detector 6 into the storage 17 as measurement data, and resets the count value of the counter to an initial value (Step #8). Then, the routine proceeds to Step #9.

In Step #9, the main controller 16 judges whether the measurement is to be continued. If it is judged that the measurement is to be continued (YES in Step #9), the routine returns to Step #4. If, on the other hand, it is judged that the measurement is not be continued (NO in Step #9), the main controller 16 performs a process of acquiring information concerning an SpO$_2$ and a blood vessel age, using the measurement data stored in the storage 17 (Step #10). The acquired information concerning the SpO$_2$ and the blood vessel age may be stored in the storage 17.

Then, if it is judged that the first display mode is selected by the blood vessel age indication button 10 (YES in Step #11), the main controller 16 controls the display section 8 to exclusively display the blood vessel age out of the information concerning the blood oxygen saturation and the blood vessel age (Step #12). If it is judged that the second display mode is selected by the oxygen saturation indication button 11 (NO in Step #11, and YES in #13), the main controller 16 controls the display section 8 to exclusively display the blood oxygen saturation out of the information concerning the blood oxygen saturation and the blood vessel age (Step #14). If it is judged that the third display mode is selected by the all indication button 12 (NO in Step #11 and NO in Step #13), the main controller 16 controls the display section 8 to display both the blood oxygen saturation and the blood vessel age (Step #15).

As mentioned above, the red LED 5a is controlled to emit light with the sampling frequency f1, and the infrared LED 5b is controlled to emit light with the sampling frequency f2 (>f1). Also, substantially all the measurement data obtained based on the output light from the red LED 5a, and the measurement data extracted at every predetermined cycle corresponding to the sampling frequency f1 of the red LED 5a out of the measurement data obtained based on the output light from the infrared LED 5b are used to acquire the SpO$_2$ data i.e. the information concerning the blood oxygen saturation, and substantially all the measurement data obtained based on the output light from the infrared LED 5b are used to acquire the information concerning the blood vessel age. This arrangement enables to realize a pulse oximeter capable of obtaining information concerning an SpO$_2$ and a blood vessel age in pair.

Also, the red LED 5a for generating measurement data which is not used in measuring the blood vessel age is controlled to emit light with the sampling frequency that is lower than the sampling frequency of the infrared LED 5b for generating measurement data used in measuring the blood vessel age, and that is sufficient for securing precision required in acquiring the SpO$_2$ data. This allows for suppressing power consumption, as compared with a case where an emission operation of the red LED 5a and an emission operation of the infrared LED 5b are conducted with sampling frequencies identical to each other.

Further, since the red LED 5a and the infrared LED 5b are controlled to emit the respective light with phases displaced from each other, there is no likelihood that the light detector 6 may fail to discriminate light from the red LED 5a from light from the infrared LED 5b resulting from simultaneous emissions of the red LED 5a and the infrared LED 5b, which may result in acquisition of erroneous measurement data.

Furthermore, the sampling frequency f2 of the infrared LED 5b is set to an integral multiplication of the sampling frequency f1 of the red LED 5a. This arrangement enables to simplify the process of limitedly using the measurement data obtained based on the output light from the infrared LED 5b in acquiring the $SpO_2$ data, as compared with a case that the sampling frequency f2 of the infrared LED 5b is not equal to an integral multiplication of the sampling frequency f1 of the red LED 5a. This enables to facilitate designing a program for functioning the main controller 16 as the $SpO_2$ acquirer 19.

Also, the operation button group 9 is provided to arbitrarily change over the display of the pulse oximeter 1 between simultaneous display of the blood oxygen saturation and the blood vessel age, and selective display of the blood oxygen saturation or the blood vessel age. This enables to provide the user of the pulse oximeter 1 including the subject with intended display contents i.e. a measurement result.

Also, since the acquired information concerning the $SpO_2$ and the blood vessel age is storable into the storage 17, information concerning the $SpO_2$ and the blood vessel age can be provided to the user of the vital information measuring device even if a certain time has elapsed after the completion of acquisition of the information concerning the $SpO_2$ and the blood vessel age. This arrangement enables the user to confirm the $SpO_2$ and the blood vessel age that have been acquired in the past. This also enables to transfer the information concerning the $SpO_2$ and the blood vessel age to another electronic device such as a personal computer. This is advantageous in utilizing the inventive vital information measuring device for various purposes such as providing statistical data relating to the $SpO_2$ and the blood vessel age, including the acquired information concerning the $SpO_2$ and the blood vessel age, or printing the statistical data, using the electronic device.

The following modifications (1) through (3) may be applied to the invention in addition to or in place of the foregoing embodiment.

(1) In the foregoing embodiment, the red LED 5a is controlled to emit light with the sampling frequency f1 e.g. 30 Hz, and the infrared LED 5b is controlled to emit light with the sampling frequency f2 e.g. 120 Hz, which is higher than the sampling frequency f1. Alternatively, the red LED 5a for emitting red light R of the wavelength λ1 in the red light region may be controlled to emit light with a sampling frequency f3 e.g. 120 Hz, and the infrared LED 5b for emitting infrared light IR of the wavelength λ2 in the infrared region may be controlled to emit light with a sampling frequency f4 e.g. 30 Hz by implementing the equation: f4=(1/m)×f3 where "m" is an integer. Then, substantially all the measurement data based on the output light from the infrared LED 5b, and the measurement data extracted at every predetermined cycle corresponding to the sampling frequency f4 of the infrared LED 5b out of the measurement data obtained based on the output light from the red LED 5a may be used in acquiring the $SpO_2$ data i.e. the information concerning the blood oxygen saturation, and substantially all the measurement data obtained based on the output light from the red LED 5a may be used in acquiring the information concerning the blood vessel age.

(2) The foregoing embodiment describes the arrangement, in which the blood vessel age information is acquired as the measurement contents obtained by outputting light of a single wavelength or white light with the sampling frequency higher than the sampling frequency of the light for measuring $SpO_2$. Alternatively, information concerning an autonomic disorder or a like disorder may be acquired as the measurement contents. For instance, diagnosing the autonomic disorder requires precise reading of variations in pulse wave peak-to-peak intervals shown in FIG. 9. Accordingly, similarly to the measurement of the blood vessel age, measurement data obtained based on the output light of the sampling frequency higher than the sampling frequency of the light used in measuring $SpO_2$ is required. In the conventional pulse oximeter, a pulse rate is simultaneously measured/displayed along with the $SpO_2$. However, since the sampling frequency used in measuring the $SpO_2$ is relatively low, desirable measurement precision is not obtained if the pulse rate is unduly high e.g. 250 pulses per minute. In view of this, a pulse waveform obtained based on light with a relatively high sampling frequency may be used in computing a pulse rate.

The embodiment may include an arrangement of obtaining a photoelectric pulse waveform for use in measuring a blood vessel age or diagnosing an autonomic disorder, even if the embodiment does not embrace an arrangement of measuring a blood vessel age or diagnosing an autonomic disorder.

(3) The embodiment is not limited to the pulse oximeter, but is applicable to other measuring device such as a photoelectric pulse wave sensor.

The aforementioned embodiment essentially includes the invention having the following arrangements.

An aspect of the invention is directed to a vital information measuring device comprising: a first light emitter for outputting light having a first wavelength; a second light emitter for outputting light having a second wavelength different from the first wavelength; a light detector for detecting the light outputted from the first light emitter and the light outputted from the second light emitter; an emission controller for controlling the first light emitter and the second light emitter to emit the respective light at sampling frequencies different from each other based on a certain relationship between an emission timing of the first light emitter and an emission timing of the second light emitter; a detection controller for controlling the light detector to detect the light from the first light emitter and the light from second light emitter in synchronism with the emission timing of the first light emitter and the emission timing of the second light emitter, respectively; and a storage for storing therein a light detection signal outputted from the light detector as measurement data.

In the above arrangement, the first light emitter and the second light emitter are controlled to emit the respective light at the sampling frequencies different from each other based on the certain relationship between the emission timing of the first light emitter and the emission timing of the second light emitter. This enables to measure a photoelectric pulse waveform for assessment of a blood vessel age i.e. an arteriosclerosis index based on the light outputted from the light emitter having the higher sampling frequency, and enables to measure a blood oxygen saturation based on the part of the light outputted from the light emitter having the higher sampling frequency, and on the light outputted from the light emitter having the lower sampling frequency.

In the above arrangement, the first light emitter and the second light emitter are controlled to emit the respective light with the sampling frequencies different from each other in measuring the blood oxygen saturation. With this arrangement, substantially all the measurement data obtained based on the light from the light emitter having the lower frequency are used in acquiring information concerning the blood oxygen saturation. This eliminates an output operation of unnecessary light. Accordingly, the arrangement contributes to suppression of power consumption, as compared with a case that the first and the second light emitters emit respective light with a relatively high sampling frequency.

The above arrangement enables to realize a vital information measuring device capable of suppressing power consumption, and acquiring the photoelectric pulse waveform for use in assessment of the blood vessel age i.e. the arteriosclerosis index, and the blood oxygen saturation in pair.

In the above arrangement, preferably, the emission controller may control the first light emitter and the second light emitter to emit the respective light at the respective emission timings with phases displaced from each other.

In the above arrangement, the first light emitter and the second light emitter are controlled to emit the respective light at the respective emission timings with the phases displaced from each other. According to the above arrangement, the light detector is operative to discriminate the light outputted from the first light emitter from the light outputted from the second light emitter. This enables to eliminate a drawback that erroneous measurement data is obtained when the first and the second light emitters simultaneously emit the respective light.

In any one of the above arrangements, preferably, the emission controller may set the sampling frequency of one of the first light emitter and the second light emitter which is higher than the sampling frequency of the other one of the first light emitter and the second light emitter to an integral multiplication of the lower sampling frequency.

If the higher sampling frequency is not set to an integral multiplication of the lower sampling frequency, it is necessary to perform an interpolation with respect to measurement data in obtaining the measurement data at the cycle corresponding to the lower sampling frequency, which makes the process of acquiring the information concerning the blood oxygen saturation complicated.

On the other hand, setting the higher sampling frequency to the integral multiplication of the lower sampling frequency, as proposed in the arrangement of the embodiment, is free from the drawback that the process of acquiring the information concerning the blood oxygen saturation may be made complicated for the following reason. Measurement data is obtained at the cycle corresponding to the lower sampling frequency, out of the measurement data obtained based on the emission operation of the light emitter having the higher sampling frequency, by merely extracting the part of the measurement data out of the measurement data which is stored in the storage and which is obtained based on the emission operation of the light emitter having the higher sampling frequency.

According to the above arrangement, the complication of the process for acquiring the information concerning the blood oxygen saturation can be avoided. This enables to facilitate designing a program for allowing the vital information measuring device to execute the above process, and to prevent or suppress cost increase of the vital information measuring device.

In any one of the above arrangements, the vital information measuring device may preferably further comprise: a first analyzer for performing a first analysis based on the measurement data obtained by using the one of the first light emitter and the second light emitter having the higher sampling frequency, out of the measurement data stored in the storage.

In the above arrangement, the first analysis is performed based on the measurement data obtained by using the light emitter having the higher sampling frequency, out of the measurement data stored in the storage. This enables to measure a photoelectric pulse waveform for use in assessment of the blood vessel age i.e. the arteriosclerosis index or a like parameter.

In any one of the above arrangements, preferably, the vital information measuring device may further comprise: a second analyzer for performing a second analysis based on the measurement data obtained by using the other one of the first light emitter and the second light emitter having the lower sampling frequency, out of the measurement data stored in the storage, and based on the measurement data which is extracted at a predetermined time interval corresponding to the lower sampling frequency, out of the measurement data obtained by using the one of the first light emitter and the second light emitter having the higher sampling frequency.

In the above arrangement, the second analysis is performed based on the measurement data obtained by using the light emitter having the lower sampling frequency, out of the measurement data stored in the storage, and based on the measurement data which is extracted at the predetermined time interval corresponding to the lower sampling frequency, out of the measurement data obtained by using the light emitter having the higher sampling frequency. This enables to measure a blood oxygen saturation.

In the above arrangement, preferably, the vital information measuring device may further comprise: a display section for displaying an analysis result of the first analyzer and an analysis result of the second analyzer; a display mode changer for changing over a display concerning the analysis result of the first analyzer and the analysis result of the second analyzer among a first display mode of exclusively displaying the analysis result of the first analyzer, a second display mode of exclusively displaying the analysis result of the second analyzer, and a third display mode of displaying both the analysis result of the first analyzer and the analysis result of the second analyzer; and a display controller for controlling the display section to display the analysis result in the display mode selected by the display mode changer.

In the above arrangement, in response to selection of the first display mode by the display mode changer, the analysis result of the first analyzer is exclusively displayed on the display section, out of the analysis result of the first analyzer and the analysis result of the second analyzer. In response to selection of the second display mode by the display mode changer, the analysis result of the second analyzer is exclusively displayed on the display section, out of the analysis result of the first analyzer and the analysis result of the second analyzer. In response to selection of the third display mode by the display mode changer, both the analysis result of the first analyzer and the analysis result of the second analyzer are displayed on the display section. With this arrangement, the user of the vital information measuring device is informed of the display contents as intended.

The above arrangement enables to realize a vital information measuring device that allows the user to display the measurement result in an intended display format.

In the above arrangement, preferably, the storage may store therein the analysis result of the first analyzer and the analysis result of the second analyzer.

In the above arrangement, since the storage stores therein the analysis result of the first analyzer and the analysis result of the second analyzer, the analysis results can be provided to the user of the vital information measuring device even if a certain time has lapsed after completion of the analyses by the first and the second analyzers, and the analysis results can be transferred to another electronic device such as a personal computer.

According to the above arrangement, the analysis result can be provided to the user of the vital information measuring device even if the certain time has lapsed after the completion of the analyses by the first and the second analyzers. This allows the user to confirm the analysis results that have been obtained in the past, and enables to transfer the analysis results to the another electronic device such as the personal computer. Thus, the analysis results are made usable for versatile purposes.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A vital information measuring device comprising:
    a first light emitter for outputting light having a first wavelength;
    a second light emitter for outputting light having a second wavelength different from the first wavelength;
    a light detector for detecting the light outputted from the first light emitter and the light outputted from the second light emitter;
    an emission controller for controlling the first light emitter to emit the light at a first sampling frequency and the second light emitter to emit the light at a second sampling frequency based on a relationship between an emission timing of the first light emitter and an emission timing of the second light emitter having phases displaced from each other, wherein the emission controller sets the first sampling frequency to an integral multiple of the second sampling frequency using an integer greater than one;
    a detection controller for controlling the light detector to detect the light from the first light emitter and the light from second light emitter in synchronism with the emission timing of the first light emitter and the emission timing of the second light emitter, respectively; and
    a storage for storing therein a light detection signal outputted from the light detector as measurement data;
    a first analyzer for performing a first analysis based on only first measurement data obtained by using the first light emitter and stored in the storage; and
    a second analyzer for performing a second analysis based on second measurement data obtained by using the second light emitter and stored in the storage, and third measurement data which is extracted out of the first measurement data at a predetermined time interval corresponding to the second sampling frequency.

2. The vital information measuring device according to claim 1, further comprising:
    a display section for displaying an analysis result of the first analyzer and an analysis result of the second analyzer;
    a display mode changer for changing over a display concerning the analysis result of the first analyzer and the analysis result of the second analyzer among a first display mode of exclusively displaying the analysis result of the first analyzer, a second display mode of exclusively displaying the analysis result of the second analyzer, and a third display mode of displaying both the analysis result of the first analyzer and the analysis result of the second analyzer; and
    a display controller for controlling the display section to display the analysis result in the display mode selected by the display mode changer.

3. The vital information measuring device according to claim 1, wherein
    the storage stores therein the analysis result of the first analyzer and the analysis result of the second analyzer.

4. A vital information measuring device comprising:
    a first light emitter for outputting light having a first wavelength at a first frequency;
    a second light emitter for outputting light having a second wavelength different from the first wavelength at a second frequency different from the first frequency;
    a light detector for detecting the light outputted from the first light emitter and the light outputted from the second light emitter;
    a first analyzer for performing a first analysis based on first measurement data obtained by using the first light emitter and sampled at the first frequency; and
    a second analyzer for performing a second analysis based on both second measurement data obtained by using the second light emitter and third measurement data which is extracted out of the first measurement data at a predetermined time corresponding to the second frequency;
    wherein the first frequency is set to an integral multiple of the second frequency using an integer greater than one.

* * * * *